US 9,763,816 B2

(12) United States Patent
Roeder

(10) Patent No.: US 9,763,816 B2
(45) Date of Patent: Sep. 19, 2017

(54) ENDOLUMINAL PROSTHESIS DELIVERY SYSTEM AND METHOD

(71) Applicant: Cook Medical Technologies LLC, Bloomington, IN (US)

(72) Inventor: Blayne A. Roeder, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 779 days.

(21) Appl. No.: 13/837,051

(22) Filed: Mar. 15, 2013

(65) Prior Publication Data

US 2014/0277362 A1  Sep. 18, 2014

(51) Int. Cl.
*A61F 2/97* (2013.01)
*A61F 2/954* (2013.01)
(Continued)

(52) U.S. Cl.
CPC .............. *A61F 2/954* (2013.01); *A61F 2/966* (2013.01); *A61F 2/97* (2013.01); *A61F 2/07* (2013.01);
(Continued)

(58) Field of Classification Search
CPC .. A61F 2/954; A61F 2/966; A61F 2/97; A61F 2/07; A61F 2/89; A61F 2230/0054;
(Continued)

(56) References Cited

U.S. PATENT DOCUMENTS

| 5,562,726 A | 10/1996 | Chuter |
| 5,662,675 A | 9/1997 | Polanskyj Stockert et al. |

(Continued)

FOREIGN PATENT DOCUMENTS

| AU | WO98/53761 | 3/1998 |
| WO | 00/42948 A2 | 7/2000 |
| WO | 2012/106491 A1 | 8/2012 |

OTHER PUBLICATIONS

Resch et al., European Journal of Vascular and Endovascular Surgery 43 (2012) vol. 43, pp. 655-660, Development of Off-the-shelf Stent Grafts for Juxtarenal Abdominal Aortic Aneurysms, Feb. 18, 2012.
(Continued)

*Primary Examiner* — Corrine McDermott
*Assistant Examiner* — Tin Nguyen
(74) *Attorney, Agent, or Firm* — Brinks Gilson & Lione

(57) ABSTRACT

A first endoluminal prosthesis coupled to an inner catheter and a dilator tip is delivered to the body vessel via a guidewire and a delivery sheath in a conventional manner. After deployment of the first endoluminal prosthesis at the target site, the dilator and catheter are retracted from the body, leaving the delivery sheath in place. A second endoluminal prosthesis is housed within a peel-away sheath without a catheter or dilator tip, and is mated to the delivery sheath outside the patient. The second prosthesis is advanced from the peel-away sheath into the delivery sheath without the use of a dilator tip or catheter. As the second prosthesis is advanced into the delivery sheath from the peel-away sheath, the peel-away sheath is peeled away. The second prosthesis is advanced through the delivery sheath and delivered into an overlapping engagement with the first prosthesis.

20 Claims, 13 Drawing Sheets

(51) Int. Cl.
*A61F 2/966* (2013.01)
*A61F 2/07* (2013.01)
*A61F 2/89* (2013.01)
*A61F 2/06* (2013.01)
*A61F 2/95* (2013.01)

(52) U.S. Cl.
CPC ........... *A61F 2/89* (2013.01); *A61F 2002/067* (2013.01); *A61F 2002/9522* (2013.01); *A61F 2230/0054* (2013.01)

(58) Field of Classification Search
CPC ........ A61F 2002/9522; A61F 2002/067; A61F 2/2427; A61F 2/2436; A61F 2/95; A61F 2/962
See application file for complete search history.

(56) References Cited

U.S. PATENT DOCUMENTS

| | | | |
|---|---|---|---|
| 6,099,558 A | 8/2000 | White et al. | |
| 6,149,680 A | 11/2000 | Shelso et al. | |
| 6,485,513 B1 | 11/2002 | Fan | |
| 6,695,875 B2 | 2/2004 | Stelter et al. | |
| 8,016,872 B2 | 9/2011 | Parker | |
| 8,167,925 B2 | 5/2012 | Shaolian et al. | |
| 8,236,040 B2 | 8/2012 | Mayberry et al. | |
| 8,328,861 B2 | 12/2012 | Martin et al. | |
| 8,357,192 B2 | 1/2013 | Mayberry et al. | |
| 2004/0138734 A1 | 7/2004 | Chobotov et al. | |
| 2008/0071343 A1 | 3/2008 | Mayberry et al. | |
| 2009/0093873 A1 | 4/2009 | Navia | |
| 2011/0054586 A1 | 3/2011 | Mayberry et al. | |
| 2012/0330408 A1* | 12/2012 | Hillukka ............... | A61F 2/0095 623/2.11 |

OTHER PUBLICATIONS

Timothy A.M. Chuter, Seminars in Vascular Surgery (2007) vol. 20, pp. 90-96, Fenestrated and Branched Stent-Grafts for Thoracoabdominal, Pararenal and Juxtarenal Aortic Aneurysm Repair, Jun. 1, 2007.

* cited by examiner

ENDOLUMINAL PROSTHESIS DELIVERY SYSTEM AND METHOD

TECHNICAL FIELD OF INVENTION

The present embodiments relate generally to a delivery system for an endoluminal prosthesis and methods for facilitating deployment of such a system.

BACKGROUND

Using stent grafts to treat aneurysms is common in the medical field. Stent grafts are deployed by accessing a vasculature with a small incision in the skin and guiding a delivery system to the target area. This intraluminal delivery is less invasive and generally preferred over more intrusive forms of surgery. Multiple stent grafts may be implanted using intraluminal delivery to provide a system of interconnected stent grafts. Stent graft systems can be made of fenestrated stent grafts and smaller side branch stent grafts, including bifurcated components.

Aneurysms sometimes affect a vessel and its branch vessels, such as the aorta and the renal arteries or the aortic arch and the branch arteries. In such instances, a fenestrated graft can be implanted in the main vessel while smaller branch grafts can be deployed in the branch arteries. The main vessel grafts have fenestrations that correspond with the openings of the branch vessels. The smaller branch grafts are joined with the main vessel graft at the fenestrations. An additional distal graft can be implanted at the distal end of the main vessel graft, where the distal graft can be in the form of a single tube or be bifurcated to include a pair of leg portions that extend into the iliac arteries.

When the smaller branch grafts are deployed through the main graft fenestrations and into the branch arteries, portions of the branch grafts can remain disposed within the main vessel graft, extending partially across the lumen of the main graft. When the distal graft is subsequently introduced into the vessel and delivered to the main vessel graft and branch grafts, the delivery system of the distal graft can contact and possibly crush the branch grafts disposed within the main vessel graft. This can damage the branch grafts which can require time consuming repair or removal and re-deployment.

SUMMARY

A method for deploying an endoluminal prosthesis is provided, the method comprising: delivering a first endoluminal prosthesis housed within a lumen of a delivery sheath through a patient's skin and to a body vessel; exposing the first endoluminal prosthesis from a proximal end of the delivery sheath at a target location within the body vessel; expanding the first endoluminal prosthesis into engagement with a wall of the body vessel; delivering a second endoluminal prosthesis to a distal opening of the delivery sheath, wherein the second endoluminal prosthesis is housed within a peel-away sheath having at least two portions; advancing the second endoluminal prosthesis proximally relative to the peel-away sheath and into the distal opening of the delivery sheath; while advancing the second endoluminal prosthesis, peeling away the at least two portions of the peel-away sheath; advancing the second endoluminal prosthesis proximally through the delivery sheath; exposing the second endoluminal prosthesis from a proximal end of the delivery sheath; and expanding the second endoluminal prosthesis.

In another form, a method for deploying an endoluminal prosthesis is provided, the method comprising: delivering a first endoluminal prosthesis housed within a lumen of a delivery sheath through a patient's skin and to a body vessel; exposing the first endoluminal prosthesis from a proximal end of the delivery sheath at a target location within the body vessel; retracting a proximal end of the delivery sheath distally away from the distal end of the first endoluminal prosthesis after exposing the first endoluminal prosthesis; expanding the first endoluminal prosthesis into engagement with a wall of the body vessel; delivering a second endoluminal prosthesis to a distal opening of the delivery sheath, wherein the second endoluminal prosthesis is housed within a peel-away sheath having at least two portions; advancing the second endoluminal prosthesis proximally relative to the peel-away sheath and into the distal opening of the delivery sheath; while advancing the second endoluminal prosthesis, peeling away the at least two portions of the peel-away sheath; advancing the second endoluminal prosthesis proximally through the delivery sheath; exposing the second endoluminal prosthesis from a proximal end of the delivery sheath; and expanding the second endoluminal prosthesis into an overlapping engagement with the first endoluminal prosthesis.

In another form, a system for facilitating deployment of an endoluminal prosthesis is provided, the system comprising: a delivery sheath having proximal and distal ends and a lumen extending therebetween; a first endoluminal prosthesis having a compressed delivery state and an expanded state and being preloaded in the delivery state within the delivery sheath and moveable proximally relative to the delivery sheath; and a second prosthesis having a compressed delivery state and an expanded state and being preloaded in its delivery state into a peel-away sheath and moveable proximally relative to the peel-away sheath; wherein the peel-away sheath is sized and configured to mate with the delivery sheath where an inner diameter of the peel-away sheath generally corresponds to an inner diameter of the delivery sheath so that the second prosthesis is moveable from within the peel-away sheath into the delivery sheath lumen while remaining in its delivery state.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Figure 1:
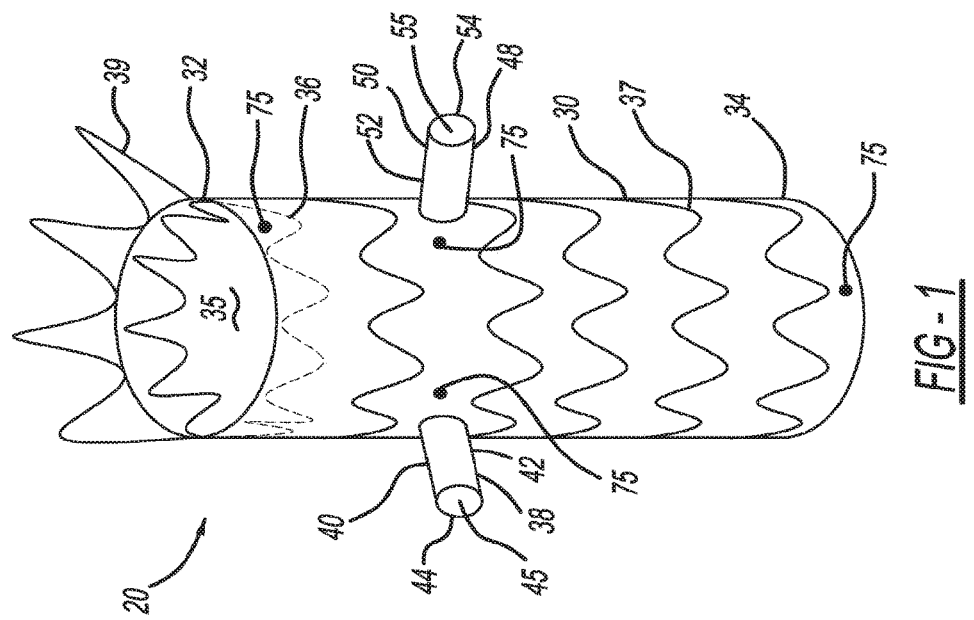
FIG. 1 is a schematic view of a first endoluminal prosthesis having branches for being coupled to corresponding branch vessels.

Referring now to FIGS. 1-14, a delivery system 10 for facilitating deployment of a first endoluminal prosthesis 20 and a second endoluminal prosthesis 25 is provided. With reference to FIG. 1, the first endoluminal prosthesis 20 comprises a graft 30 having a generally tubular body of a biocompatible material. The graft 30 has a proximal end 32, a distal end 34, and a lumen 35 extending therebetween.

The graft 30 comprises a passageway or fenestration 38 disposed in the graft 30 at a location between the proximal and distal ends 32 and 34. The passageway or fenestration 38 can be one of many known passageway or fenestration types including, but not limited to, a pivoting fenestration, an internal branch, an external branch, an external helical branch, an internal/external branch, or other known passageways that provide fluid communication from inside the lumen 35 to outside of the graft 30 so that blood flowing within the lumen 35 can pass to connected branch vessels within the body. For this discussion, the passageway or fenestration 38 will be described as an external first branch 40 having proximal and distal ends 42 and 44 and a lumen 45 extending therebetween. The first branch 40 extends radially outward from the graft 30, but may extend in a different direction. However, it will be appreciated that references to the first branch 40 can apply to other passageway or fenestration types.

In addition to the first branch 40, the graft 30 can include a second passageway or fenestration 48, described herein as a second branch 50, having proximal and distal regions 52 and 54 and a lumen 55 extending therebetween. The second branch 50 extends radially outward from the graft 30, but may extend in a different direction. Again, it will be appreciated that the second passageway or fenestration 48 could be in another form, as described above.

It will be appreciated that additional passageways or fenestrations could also be included with the graft 30, but for this discussion, the graft 30 having the first and second branches 40 and 50 will be discussed.

The graft 30 is shown as having a generally tubular shape with a generally constant diameter. It will be appreciated, however, that the outer profile, size, or shape of the graft 30 can change depending on its particular application. For example, the graft 30 could have a different diameter for different portions, or could be bifurcated with a pair of leg portions. However, for this discussion herein, the graft 30 will be described as being tubular with a generally constant diameter.

Figure 2:
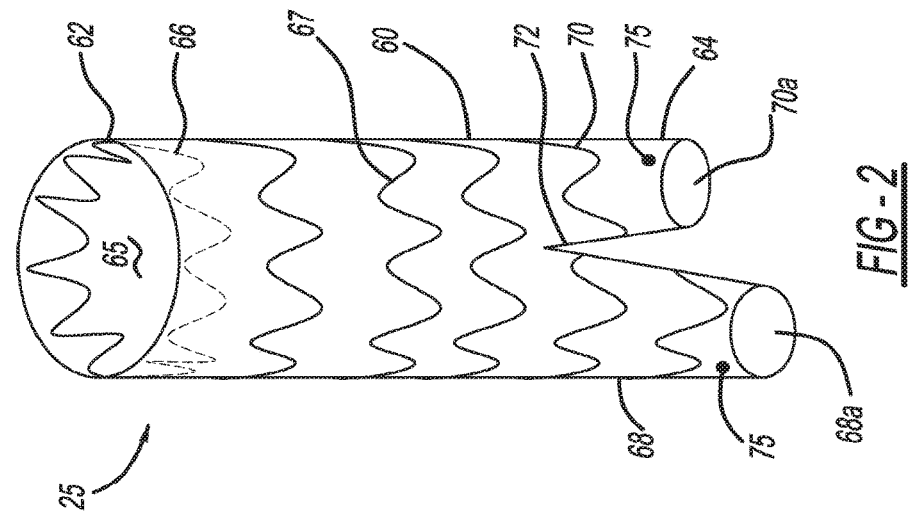
FIG. 2 is a schematic view of a second endoluminal prosthesis configured for being coupled to a distal end of the first endoluminal prosthesis.

With reference to FIG. 2, the second endoluminal prosthesis 25 can be similar to the first prosthesis 20, where the second endoluminal prosthesis 25 includes a graft 60 having a generally tubular body of a biocompatible material. The graft 60 has a proximal end 62, a distal end 64, and a lumen 65 extending therebetween. The graft 60 could be in the form of a bifurcated graft where the distal end 64 includes first and second leg portions 68 and 70, each defining a lumen 68a and 70a therethrough that combine with the lumen 65 at a bifurcation region 72. In one form, the first leg portion 68 is longer than the second leg portion 70. For this discussion, the graft 60 will be described as being bifurcated, but other shapes of the graft 60 could also be used.

Many different types of graft materials may be used for the grafts 30 and 60. Common examples of graft materials currently used include expandable polytetrafluoroethylene (ePTFE), polytetrafluoroethylene (PTFE), Dacron, polyester, fabrics and collagen. However, graft materials may be made from numerous other materials as well, including both synthetic polymers and natural tissues.

The first and second endoluminal prostheses 20 and 25 further comprise at least one stent coupled to the grafts 30 and 60, respectively. In the example of FIG. 1, a stent 36 is coupled to an inner surface of the graft 30 at a proximal region of the graft 30, while a plurality of stents 37 are coupled to an outer surface of the graft 30 along a distal region of the graft 30. A bare stent 39 can be coupled to the proximal end of the graft 30 and used for anchoring the prosthesis 20 when it is expanded in a vessel. While one exemplary arrangement is shown in FIG. 1, it will be appreciated that the stents 36 and 37 may be coupled to inner and/or outer surfaces of the graft 30, and that the prosthesis can include various combinations and relative quantities of inner and outer stents.

Similarly, as shown in FIG. 2, a stent 66 is coupled to an inner surface of the graft 60 at a proximal region of the graft 60, while a plurality of stents 67 are coupled to an outer surface of the graft 60 along a distal region of the graft 60. While one exemplary arrangement is shown in FIG. 2, it will be appreciated that the stents 66 and 67 may be coupled to inner and/or outer surfaces of the graft 30. The graft 60 can be provided without a bare stent, because the graft 60 is intended to be inserted in an overlapping configuration within the distal end of the graft 30, as further described below.

The stents 36, 37, 66, 67 may be made from numerous metals and alloys. In one example, the stents 36, 37, 66, 67 comprise a shape-memory material such as a nickel-titanium alloy ("nitinol"). Moreover, the structure of the stents 36, 37, 66, 67 may be formed in a variety of ways to provide a suitable intraluminal support structure. For example, one or more stents may be made from a woven wire structure, a laser-cut cannula, individual interconnected rings, or another pattern or design.

In one example, shown in FIGS. 1 and 2, the stents 36, 37, 66, 67 may be configured in the form of one or more "Z-stents" or Gianturco stents, each of which may comprise a series of substantially straight segments interconnected by a series of bent segments. The bent segments may comprise acute bends or apices. The Gianturco stents are arranged in a zigzag configuration in which the straight segments are set at angles relative to each other and are connected by the bent segments. However, as noted above, the stents 36, 37, 66, 67 may comprise any suitable configuration, and one or more stents may be provided. The bare stent 39 of the prosthesis 20 can be similarly constructed, and its distal end can be coupled to the proximal end of the graft 30 such that the bare stent 39 will open outward at its proximal end to anchor the prosthesis 20.

The graft 30 has a compressed, reduced diameter delivery state, shown in FIG. 3, in which it may be advanced to a target location within a vessel, duct or other anatomical site, such as the abdominal aorta in the example of FIGS. 5-14 below. The graft 30 further has an expanded state, as shown in FIGS. 1 and 6-9, 13, and 14, in which it may be configured to apply a radially outward force upon the vessel, duct or other target location. In the expanded state, fluid flow is allowed through the lumen 35 of the graft 30 and through the branches 40 and 50 into corresponding branch vessels.

Similarly, the graft 60 has a compressed, reduced diameter delivery state, shown in FIG. 4 in which it may be advanced to a target location within a vessel, duct or other anatomical site, such as the abdominal aorta in the example of FIGS. 5-14 below. The graft 60 further has an expanded state, as shown in FIGS. 2 and 14, in which it may be configured to apply a radially outward force upon the vessel, duct or other target location. In the expanded state, fluid flow is allowed through the lumen 65 of the graft 60.

One or more radiopaque markers may be provided to provide radiographic visualization of the position of the endoluminal prosthesis 20 when placed in the vessel or duct of a patient. A plurality of radiopaque markers 75, which according to one example may be provided in the form of gold beads, are coupled to the grafts 30 and 60 and/or stents 36, 37, 66, 67 to facilitate imaging of various desired locations along the length of the endoluminal prostheses 20 and 25.

While the above described prostheses 20 and 25 and grafts 30 and 35 thereof have been described similarly, their delivery configurations and method of delivery are performed differently, as further described below.

Figure 3:
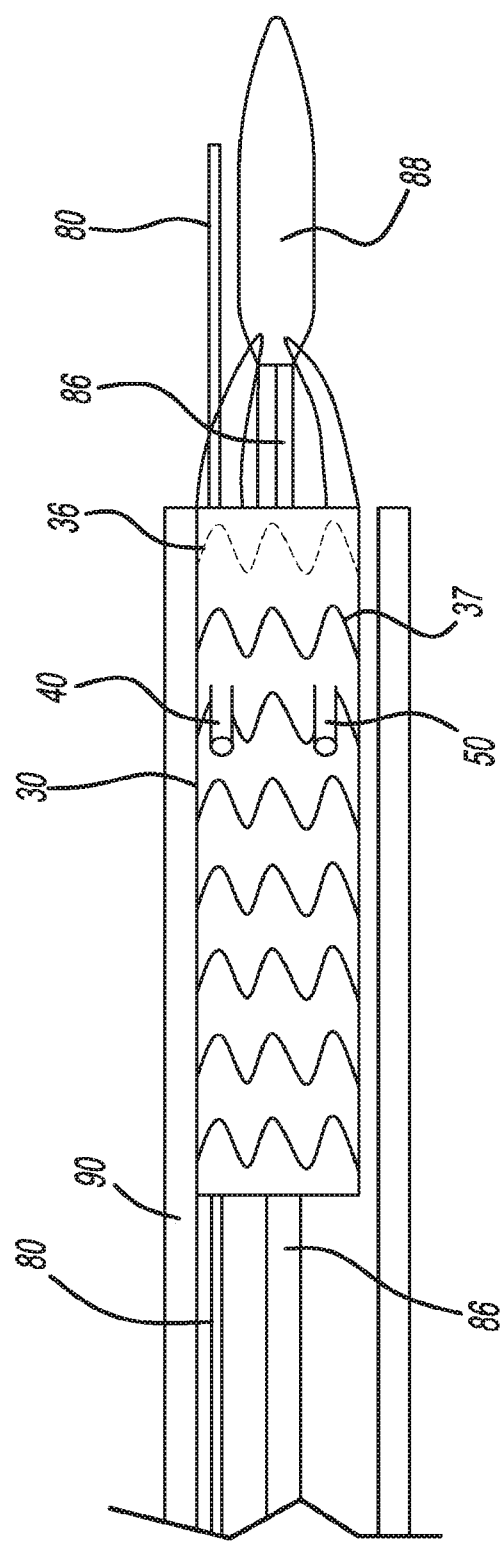
FIG. 3 is a schematic view showing the first endoluminal prosthesis in a delivery configuration, a delivery sheath surrounding the prosthesis, a catheter extending through a lumen of the prosthesis, a guidewire, and a dilator tip.

With reference to FIG. 3, the endoluminal prosthesis 20 may be provided as part of a preloaded system that can be guided along a first guidewire 80 in a manner known in the art, which is configured to facilitate insertion of at least the first prosthesis 20 and preferably the second prosthesis 25, as well. More specifically, the delivery system of the first prosthesis 20 includes the first prosthesis 20 arranged in its compressed delivery configuration, and the guidewire 80 extends through the lumen 35 along with a delivery catheter 86. A dilator tip 88 is disposed at the proximal end of the catheter 86 and proximally of the graft 30. The bare stent 39 is compressed and may be held to the dilator tip 88. In one form, the bare stent 39 is held to the dilator tip using one or more trigger wires (not shown) that can be withdrawn to release the bare stent 39. Of course, other methods of constraining the bare stent 39 can also be used. A delivery sheath 90 surrounds the graft 30 and the catheter 86 on which the graft is disposed.

Figure 4:
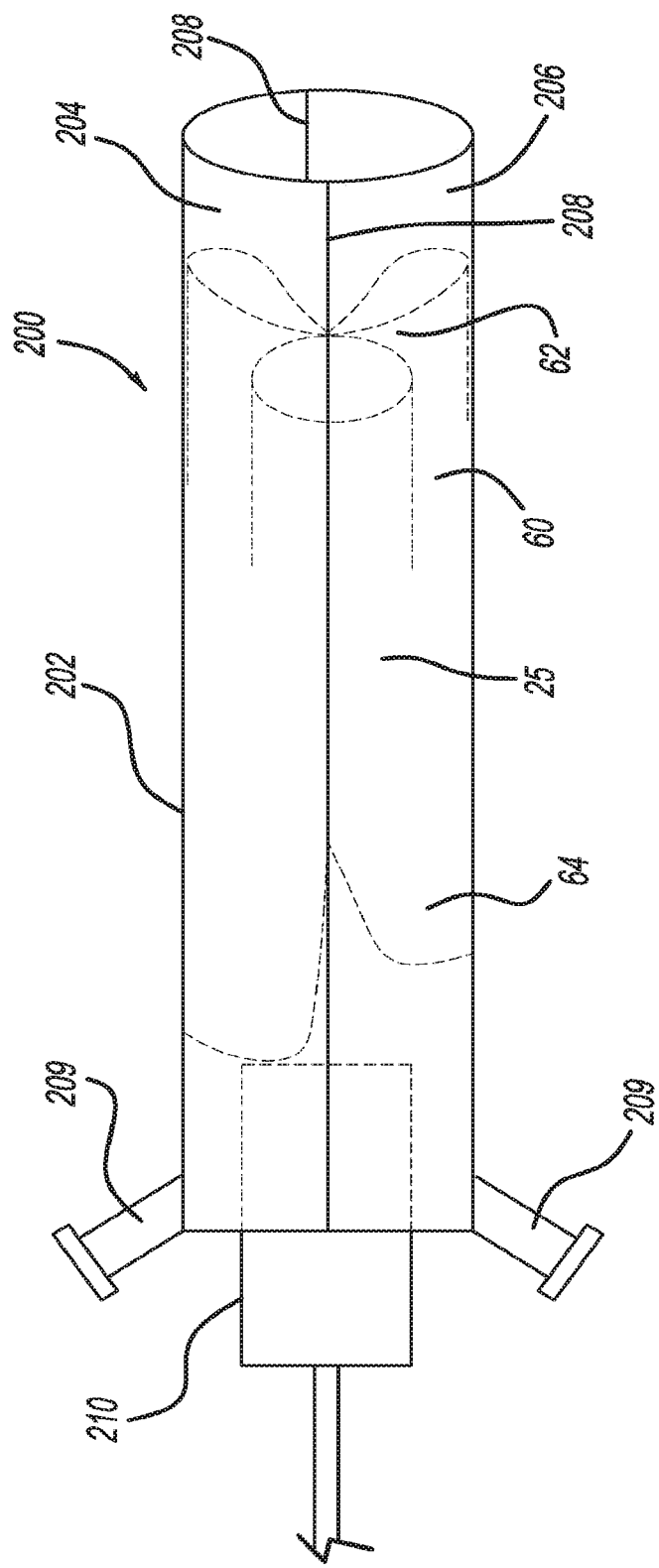
FIG. 4 is a schematic view showing the second endoluminal prosthesis in a delivery configuration, a peel-away sheath surrounding the prosthesis, and a pusher member.

With reference to FIG. 4, the prosthesis 25 can also be preloaded into a delivery device or cartridge 200. The cartridge 200 can be in the form of a peel-away sheath 202 having at least two portions 204 and 206. The peel-away sheath 202 can further include scoring 208 extending longitudinally along the length of the sheath 202 to aid in peeling the portions 204, 206 away from each other. The graft 60 can be compressed in its preloaded state using known methods for constraining a self-expanding prosthesis. In one form, the proximal end 62 of the graft 60 can be constrained in a tri-fold shape in a manner known in the art. In another form, the prosthesis 25 can be compressed radially with the graft 60 material folded over itself in a manner known in the art. The prosthesis 25 can be preloaded into the sheath 202 such that the graft material directly contacts the inner surface of the sheath 202 without an intermediate sheath between the graft 60 and the peel-away sheath 202. The prosthesis 25 can be pre-loaded into the peel-away sheath 202 without a traditional dilator tip, unlike the prosthesis 20 described above.

The peel-away sheath 202 can include a pair of tab members 209 coupled to the distal ends of portions 204, 206 to facilitate the peeling process to separate the portions 204 and 206 along the scoring 208.

Referring now to FIGS. 5-14, exemplary method steps for using the prostheses of FIGS. 1-4 to treat a condition in the area of a patient's abdominal aorta and/or branch vessels are shown and described. In a first step, the endoluminal prosthesis 20 is provided compressed into a delivery state, and is delivered into the patient's abdominal aorta using a suitable deployment system or introducer. An introducer such as that described in PCT application WO98/53761, entitled "A Prosthesis and a Method and Means of Deploying a Prosthesis," which is incorporated herein by reference in its entirety, may be used to deploy the endoluminal prosthesis 20. PCT application WO98/53761 describes a deployment system for an endoluminal prosthesis whereby the prosthesis is radially compressed onto a delivery catheter and is covered by an outer sheath.

Figure 5:
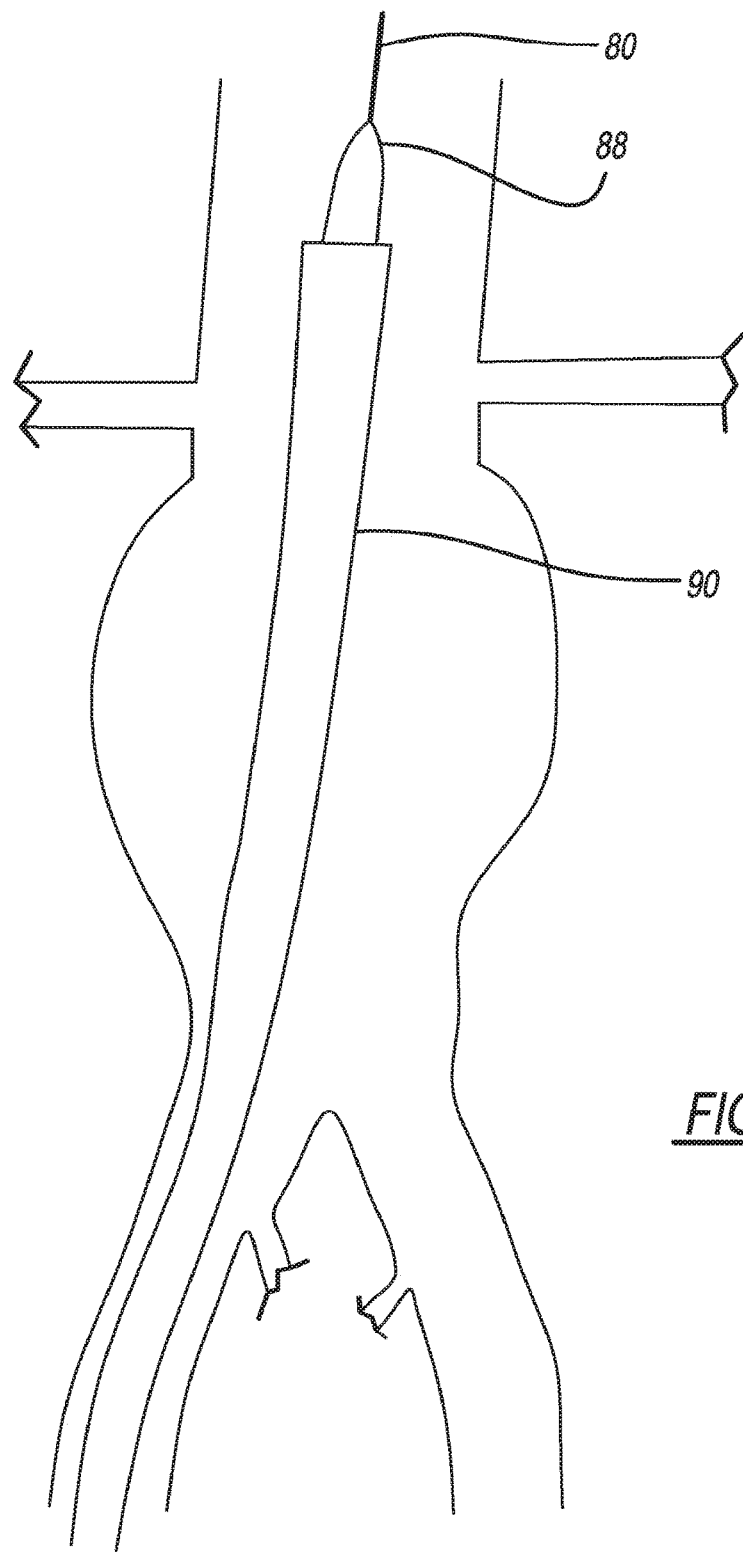
FIG. 5 is a schematic view showing the delivery sheath and dilator tip for delivering the first endoluminal prosthesis disposed at a target delivery site within a patient's body.
Figure 6:
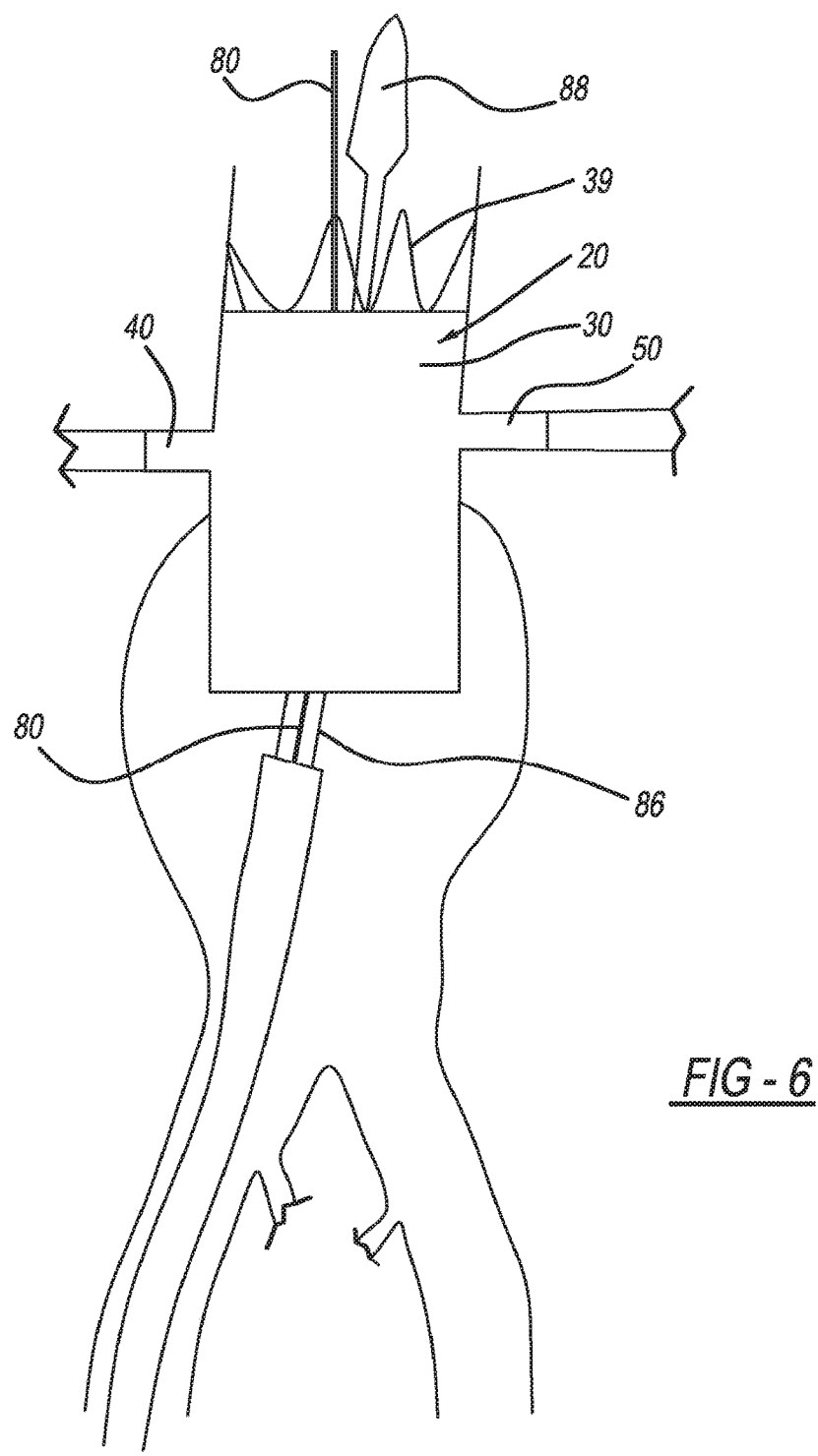
FIG. 6 is a schematic view showing the first endoluminal prosthesis exposed from the delivery sheath and delivered to the target site.

With reference to the system described above, the prosthesis 20 is introduced into the patient's body percutaneously via femoral cut-down. The guidewire 80 is introduced into the patient's body vessel and advanced toward the abdominal aorta and past the target location of the prosthesis 20. The delivery sheath 90, having the prosthesis 20, catheter 86, and dilator tip 88 is guided over the guidewire 80 and toward the target site, as shown in FIG. 5. To deploy the prosthesis 20, the operator slides or retracts the sheath 90 from the delivery catheter 86 and dilator tip 88, thereby exposing the prosthesis 20. The prosthesis 20 is self-expanding and expands outwardly upon removal of the sheath 90. The bare stent 39 can be released by manipulating the trigger wires or other known restraining mechanism, allowing the bare stent 39 to expand outwardly into engagement with the body vessel to anchor the prosthesis 20, shown delivered in FIG. 6. The operator can directly manipulate the sheath 90 and the delivery catheter 86, which provides the operator with a relatively high degree of control during the procedure. Further, such delivery devices may be compact and may have a relatively uniform, low-diameter radial profile, allowing for atraumatic access and delivery.

The endoluminal prosthesis 20 is positioned within the abdominal aorta in the compressed state, for example, using the radiopaque markers 75, such that the branches 40 and 50 are generally aligned in the vicinity of the ostiums of the desired branch vessels, such as the right renal artery, celiac artery, superior mesenteric artery, or left renal artery. At this time, the sheath 90 of the delivery system that constrains the endoluminal prosthesis 20 may be retracted distally to allow the stents 36 and 37, and the graft 30 coupled thereto, to attain the expanded deployed configuration shown in FIG. 6.

In use, the graft 30 is sized and configured so that at least an outer surface of the proximal region of the graft 30 securely engages an inner surface of the abdominal aorta to hold the graft 30 in place relative to the vasculature. The dilator tip 88 and the catheter 86 can be retracted proximally through the sheath 90 and out of the patient, leaving the sheath 90 and guidewire 80 in place.

After the graft 30 is securely deployed within the patient's abdominal aorta, in a next step, branch extension prosthesis 120 and 130 can be delivered to the graft 30 to bridge between the branches 40 and 50 into the corresponding branch vessels. Delivery of the branch extensions 120 and 130 can be performed in a manner known in the art, such as through femoral artery access, similar to the delivery of the prosthesis 20, through brachial artery access, or the like.

Figure 7:
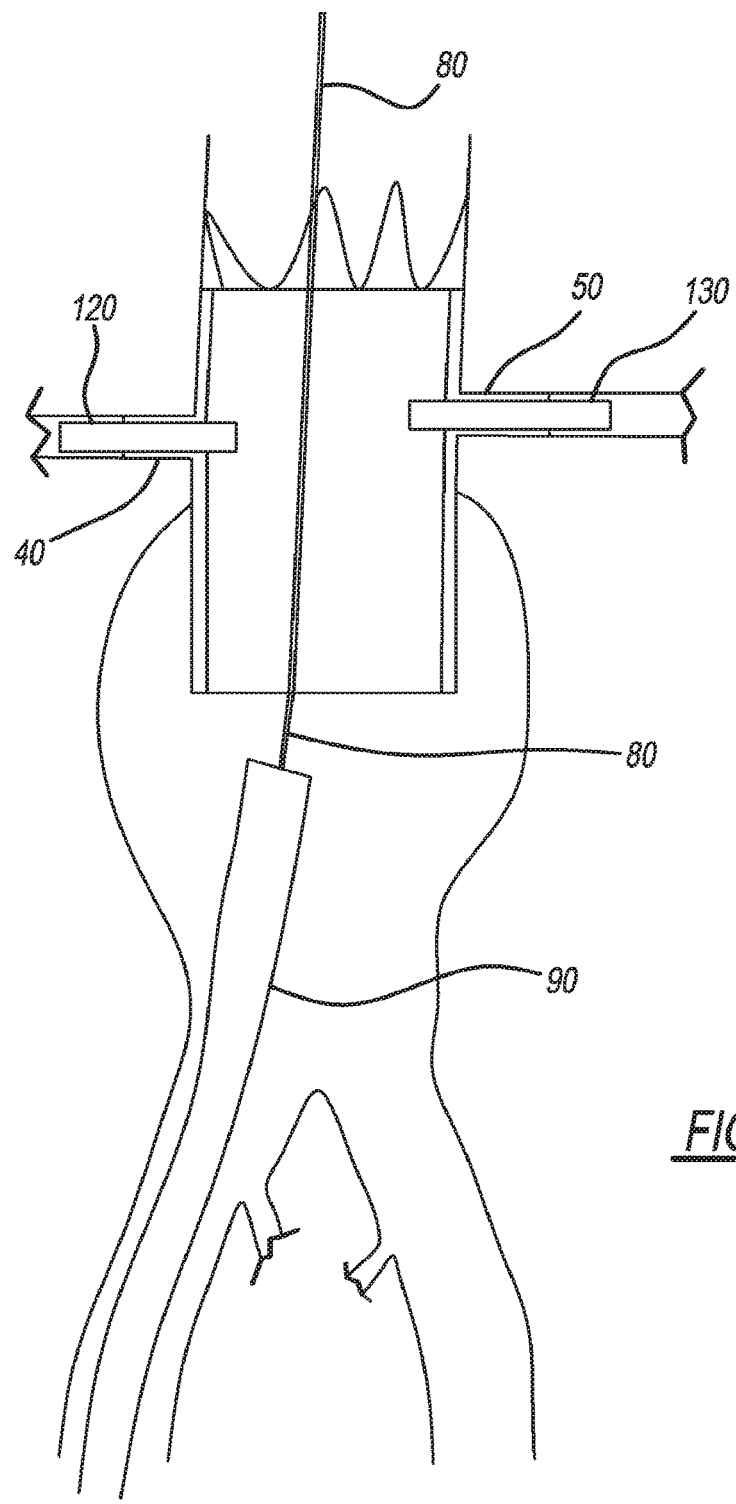
FIG. 7 is a schematic view showing a pair of branch extension prostheses delivered to bridge the branches of the first endoluminal prosthesis with corresponding branch vessels and showing the dilator tip retracted and the delivery sheath disposed adjacent the distal end of the prosthesis.

Referring to FIG. 7, upon deployment, the branch extension prosthesis 120 and the first branch 40 of the graft 30 are mated such that there is a suitable tromboning connection, preferably with a 1.5 to 2 cm overlap and a 1 mm or less difference in diameter at the interconnection. Optionally, the devices may be expanded for about 30 seconds using a suitably sized balloon dilation catheter. At this time, the branch extension prosthesis 120 provides patent fluid flow through the graft 30 into the corresponding branch vessel. The branch extension prosthesis 130 can be deployed similarly. The branch extension prostheses 120 and 130 may extend into the lumen 35 of the graft 30, as shown in FIG. 7.

The branch extension prosthesis 120, as well as the branch extension prosthesis 130, may comprise a suitable graft or stent-graft known in the art to direct flow from the graft 30 into the branch vessels.

Having deployed the prosthesis 20 and branch extensions 120 and 130, the sheath 90 has remained in place near the distal end of the graft 30. The sheath 90, after being retracted to allow the graft 30 to expand, can be held distally of the distal end of the graft 30 prior to introduction of the branch extensions 120 and 130. Alternatively, the sheath 90 can be advanced proximally back over the guidewire 80 and partially into the distal end of the graft 30 prior to introduction of the branch extensions 120 and 130.

Figure 8:
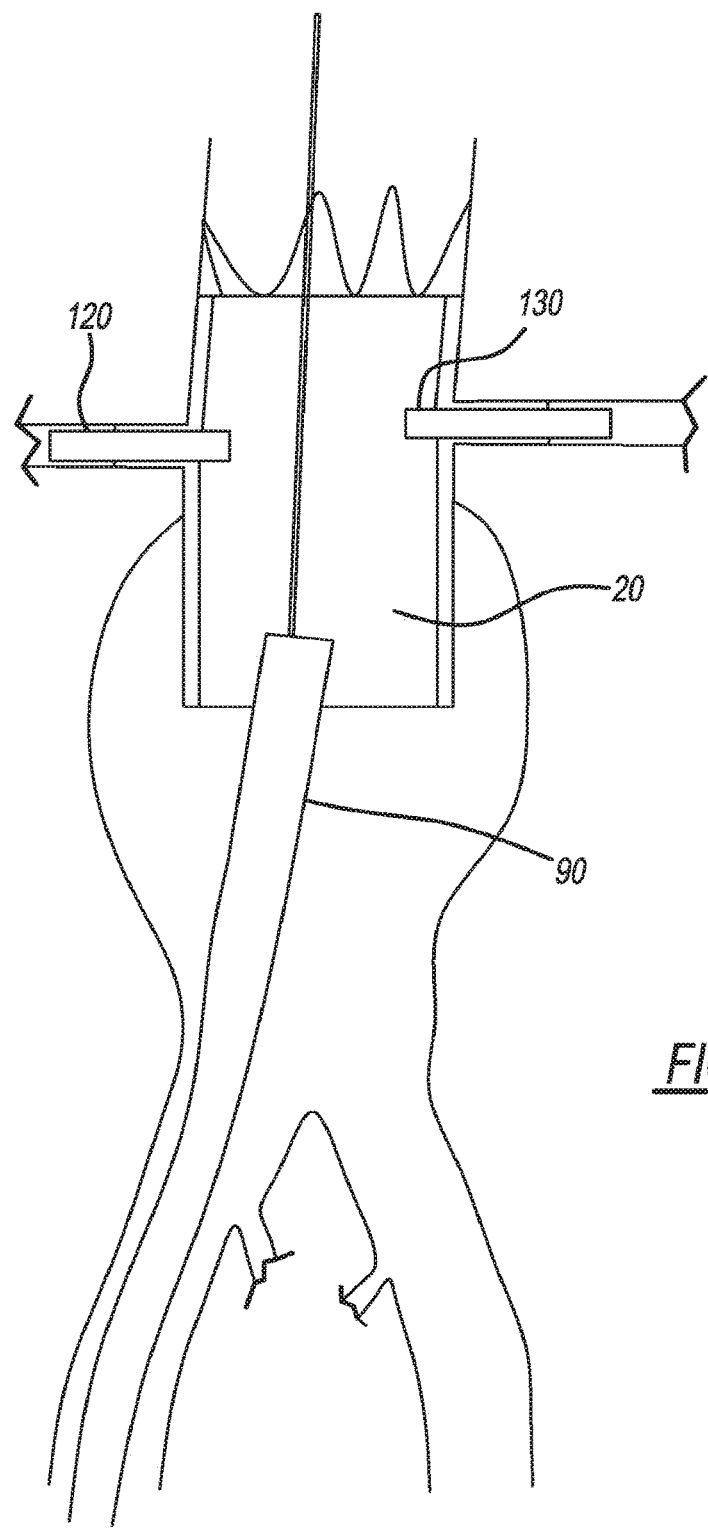
FIG. 8 is a schematic view showing the delivery sheath disposed within the distal end of the first endoluminal prosthesis.

If the sheath 90 is located distally of the graft 30, the sheath 90 can be advanced back into the graft 30, as shown in FIG. 8, so that it partially extends into the distal end of the graft 30 after the branch extensions 120 and 130 have been deployed. Alternatively, the sheath 90 can remain disposed distal of the graft 30, if desired.

Figure 9:
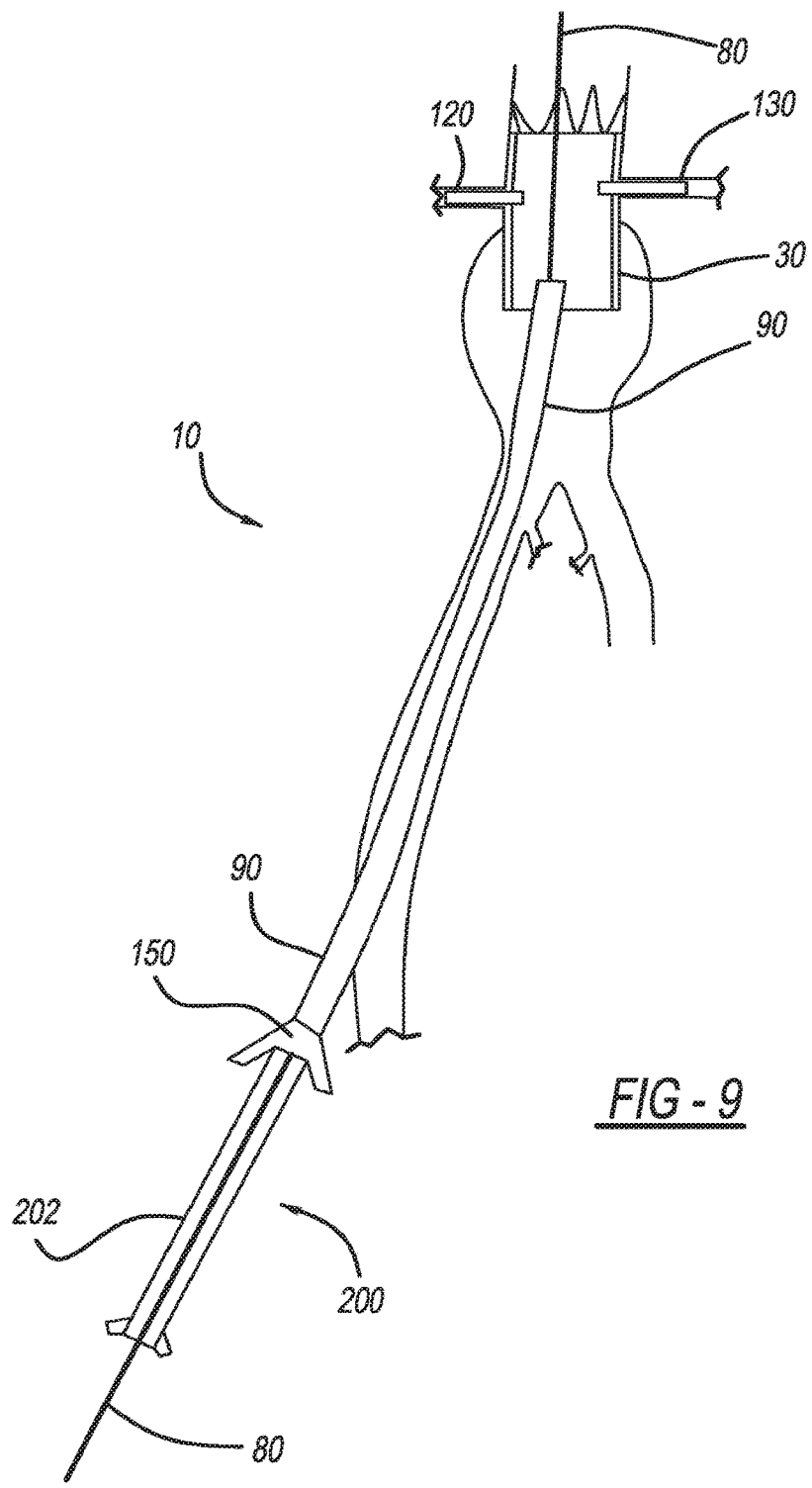
FIG. 9 is a schematic view showing the peel-away sheath coupled to the delivery sheath for delivering the second endoluminal prosthesis from the peel-away sheath into the delivery sheath.

With the proximal prosthesis 20 and branch extensions 120 and 130 being sufficiently deployed within the body vessel, the distal prosthesis 25 is delivered. The guidewire 80 and sheath 90 remain in place after delivery of the prosthesis 20, as shown in FIG. 9. The sheath 90 can include a funnel member 150 at the proximal end thereof to facilitate introduction of other components into the sheath 90.

With reference to FIG. 9, to deliver the prosthesis 25 preloaded within the peel-away sheath 202, the cartridge 200 is delivered to the funnel member 150 of the sheath 90. The cartridge 200 is placed over the guidewire 80 such that the guidewire 80 extends through the lumen 65 of the graft 60 contained within the cartridge 200. The proximal end of the peel-away sheath 202 is mated with the funnel member 150 so that the prosthesis 25 can be transferred from the peel-away sheath 202 into the sheath 90 that remained in place from the delivery of the first prosthesis 20. The peel-away sheath 202 is preferably not inserted into the delivery sheath 90, but rather will abut the distal end of the delivery sheath 90 to allow the graft 60 to be advanced from the peel-away sheath 202 into the delivery sheath 90. In this approach, the peel-away sheath 202 will not overlap the delivery sheath 90 while the graft 60 is being advanced; however, the funnel member 150 can overlap the proximal end of the peel-away sheath 202 in this arrangement. It will be appreciated, however, that some overlap between the peel-away sheath 202 and the delivery sheath 90 can occur in other approaches without substantially deviating from the principles of the invention.

Figure 10:
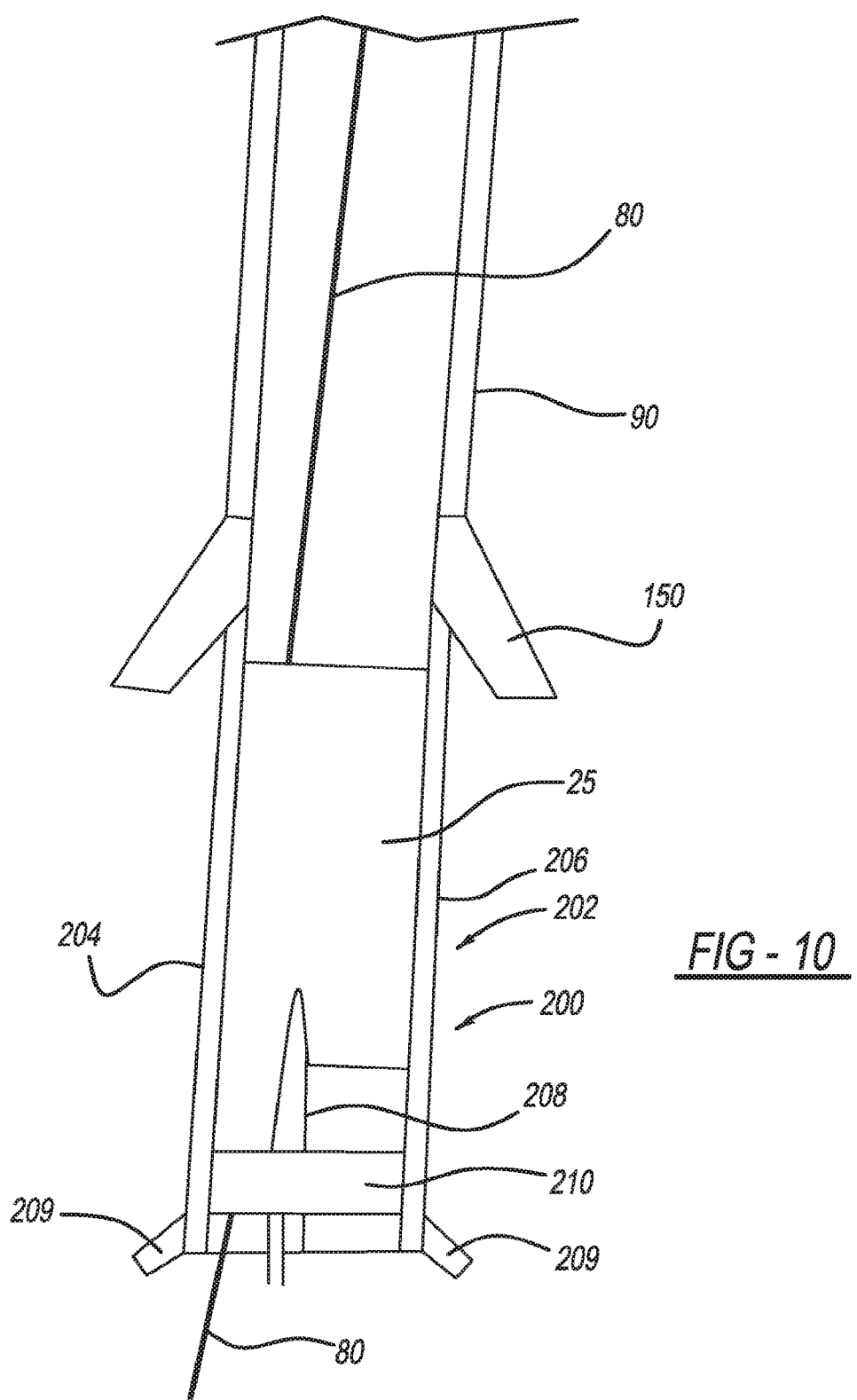
FIG. 10 is a schematic view of the second endoluminal prosthesis within the peel-away sheath prior to insertion into the delivery sheath.
Figure 11:
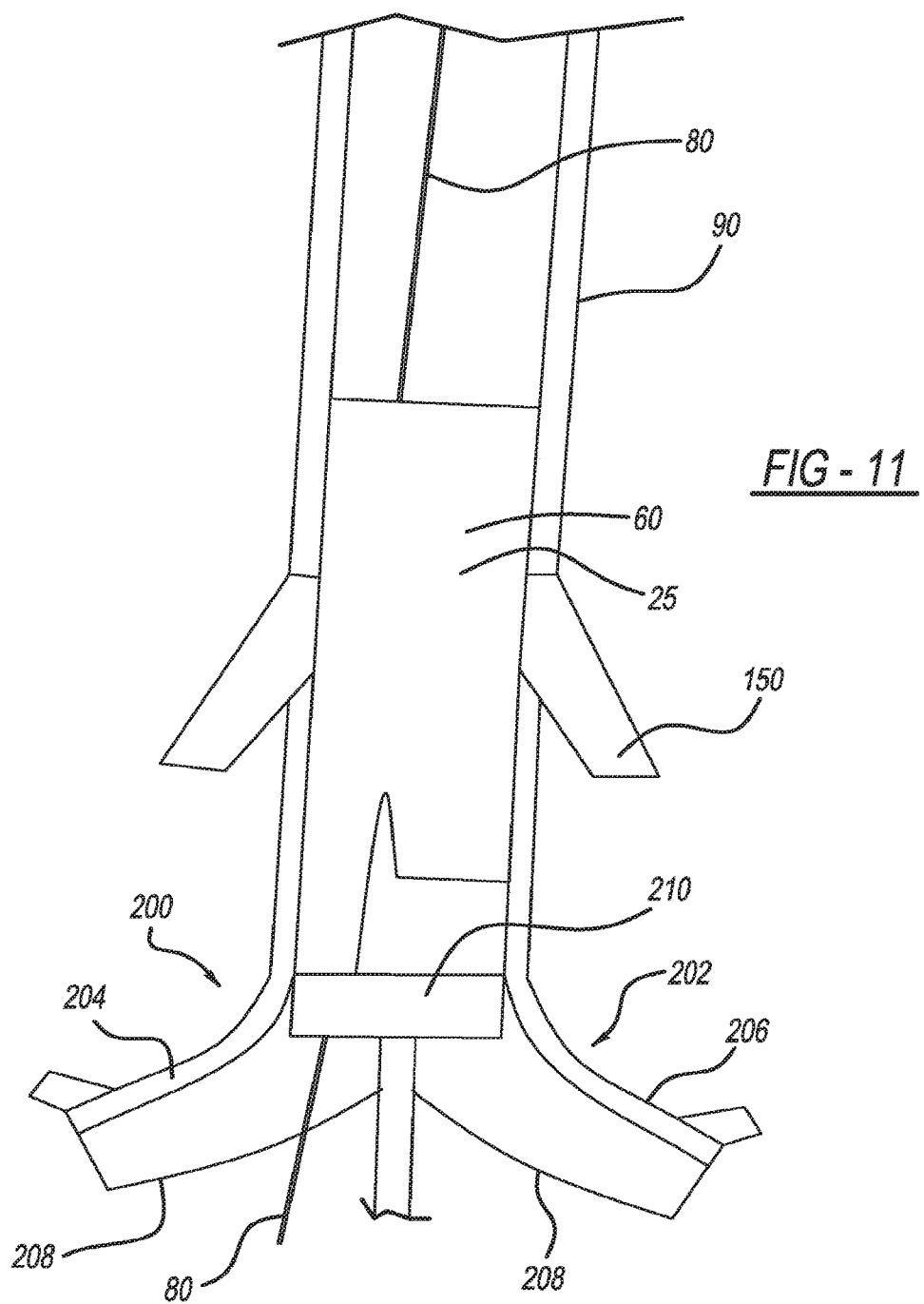
FIG. 11 is a schematic view showing the second endoluminal prosthesis partially inserted into the delivery sheath and the peel-away sheath partially peeled away.
Figure 12:
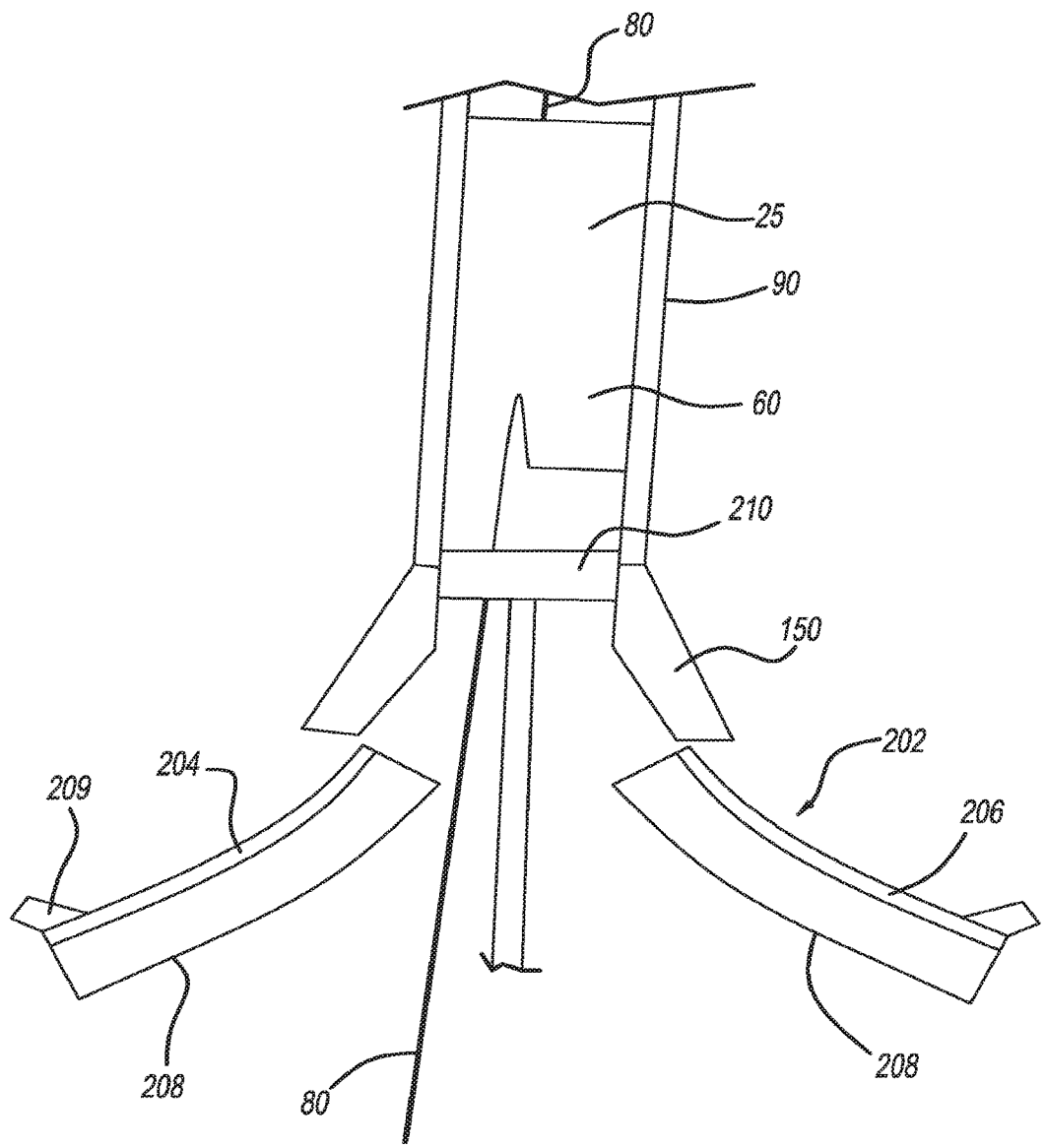
FIG. 12 is a schematic view showing the second endoluminal prosthesis fully delivered into the delivery sheath and the peel-away sheath fully peeled away.

The cartridge 200 can include a pusher member 210 (FIG. 4) positioned adjacent to the prosthesis 25 in a manner known in the art that has sufficient pushability to advance the prosthesis 25 through the peel-away sheath 202 and, subsequently, the delivery sheath 90. With reference to FIGS. 10-12, after mating the peel-away sheath 202 with the delivery sheath 90, the graft 60 can be advanced proximally from the peel-away sheath into the delivery sheath 90 by advancing the pusher member 210. The graft 60 will preferably remain in its compressed delivery configuration substantially without expanding. The inner diameter of the peel-away sheath 202 can correspond to the inner diameter of the delivery sheath 90 to facilitate keeping the graft 60 in its compressed configuration. However, it will be appreciated that some amount of expansion of the graft could also occur in the event that the inner diameter of the delivery sheath 90 is larger than the inner diameter of the peel-away sheath 202. This expansion can occur because the cartridge 200 does not include an intermediate sheath between the graft 60 and the peel-away sheath 202.

As the graft 60 is advanced into the delivery sheath 90, the portion of the peel-away sheath 202 that is no longer covering the graft 60 can be peeled away, as shown in FIG. 11. By peeling away the sheath 202, the user can maintain optimal control over the pusher member 210 near the distal end of the graft 60 to facilitate advancement of the graft 60 through the peel-away sheath 202 and into the delivery sheath 90. As the graft 60 is further advanced, the peel-away sheath 202 can be further peeled back.

Once the graft 60 has been generally fully inserted into the delivery sheath 90, as shown in FIG. 12, and the peel-away sheath 202 has been fully peeled away, the portions 204 and 206 of the peel-away sheath 202 can be discarded. The graft 60 can be further advanced through the delivery sheath 90 using the pusher member 210. The graft 60 will advanced through the sheath 90 making direct contact with the delivery sheath 90 as it is advanced.

Figure 13:
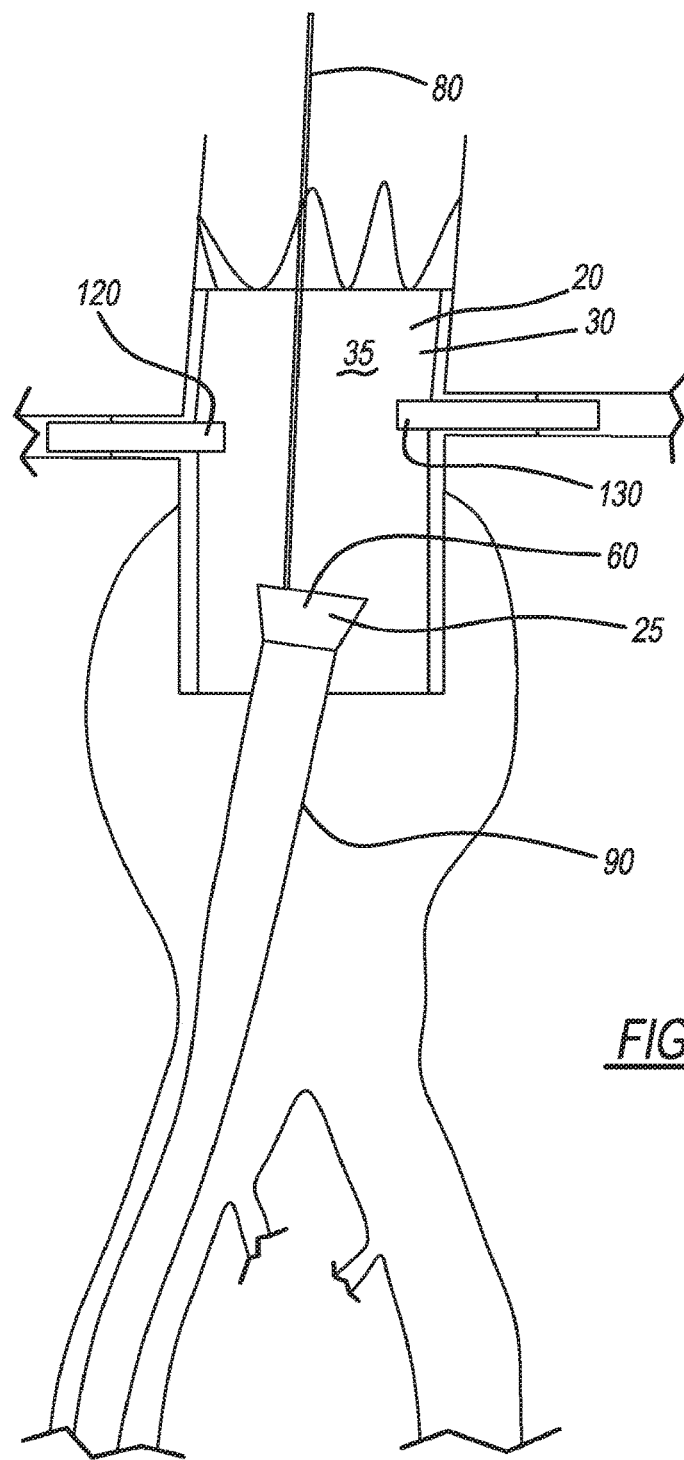
FIG. 13 is a schematic view showing the second endoluminal prosthesis partially exposed from the delivery sheath and within the distal end of the first endoluminal prosthesis.
Figure 14:
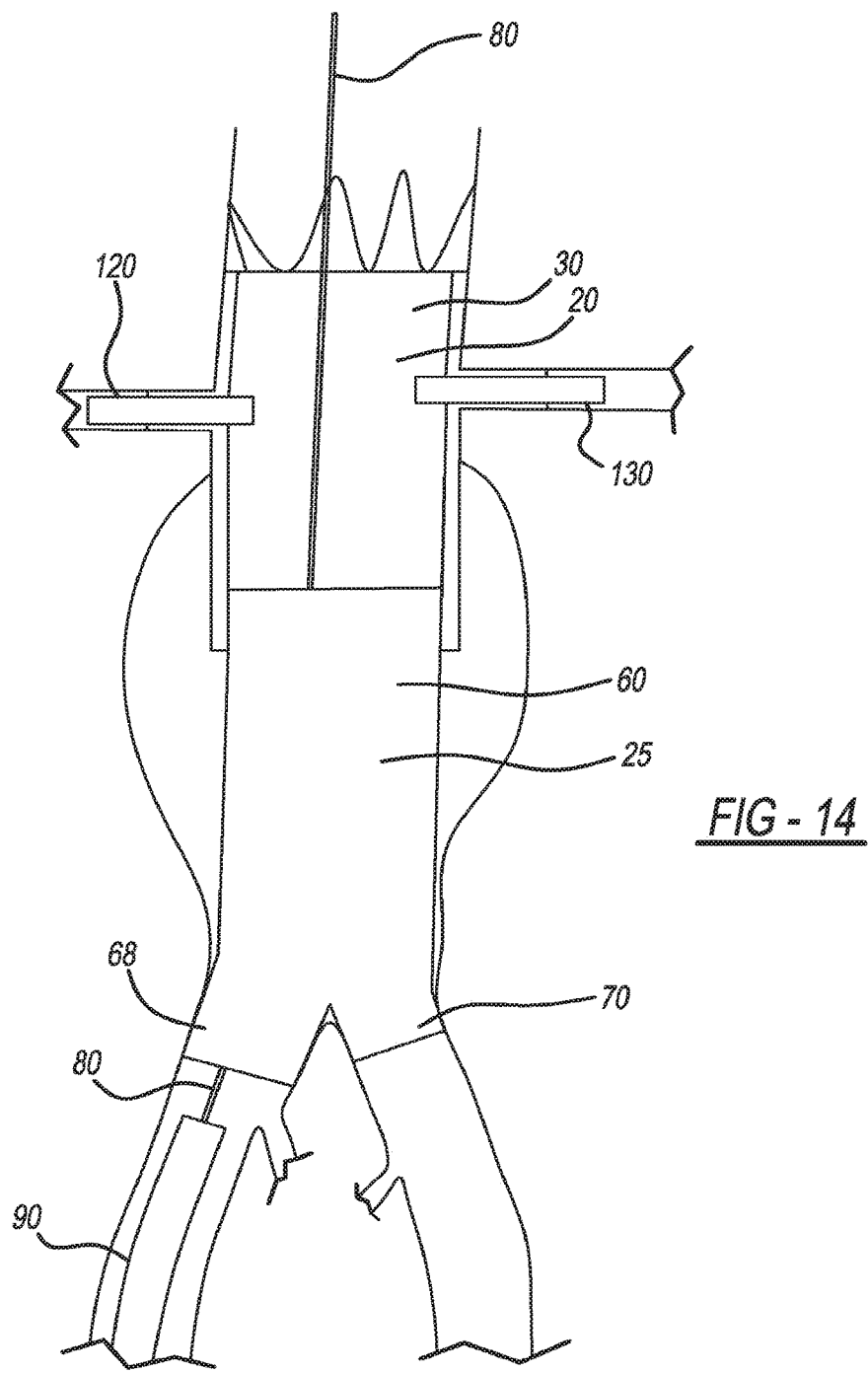
FIG. 14 is a schematic view showing the second endoluminal prosthesis fully exposed from the delivery sheath and mated with the first endoluminal prosthesis and the delivery sheath retracted distally from the prostheses.

With reference to FIG. 13, the graft 60 can be advanced through the sheath 90 and out of the sheath 90 at the distal end of the first graft 30, which has been previously deployed in the body vessel. The proximal end of the graft 60 will be exposed from the delivery sheath and overlap the distal end of the graft 30. The delivery sheath 90 is preferably disposed within the lumen 35 of the graft 30 to facilitate delivering the proximal end of the graft 60 within the lumen 35 of the graft 30.

With reference to FIG. 14, when the graft 60 becomes exposed from the sheath 90, the graft 60 will expand into engagement with the graft 30 to create an overlapping connection. The graft 60 is preferably self-expanding to facilitate this engagement. The delivery sheath 90 can then be withdrawn to expose the remainder of the graft 60 in a manner known in the art. As the sheath 90 is withdrawn, the graft 60 will expand where it has been exposed. The distal end of the graft 60 is preferably aligned within a non-diseased portion of the body vessel, so that the distal end of the graft 60 will expand into sealing engagement with the body vessel to allow blood to flow through the grafts 30 and 60 and between non-diseased portions. Alternatively, the distal end of the graft 60 can be disposed within a diseased body vessel, and an additional prosthesis can be delivered into engagement with the distal end of the graft 60 to complete the bridge between non-diseased body vessel regions.

As described above, the graft 60 can be a bifurcated graft, and the longer leg portion 68 can be disposed within one of the iliac arteries, with the shorter leg portion 70 disposed near the other iliac artery. In another form, the graft 60 can be bifurcated and include a pair of leg portions, each of which terminate prior to the iliac arteries. It will be appreciated that various shapes and types of prostheses can be delivered in the cartridge 200, and additional modular prostheses may be coupled to the graft 60, e.g., extending into the iliac arteries, whereby the modular prostheses have outer surfaces dimensioned to securely engage inner surfaces of the iliac arteries or other vasculature.

The above described delivery of the graft 60 using the cartridge 200 and peel-away sheath is different from the delivery of the graft 30 because delivery of the graft 60 did not use an inner catheter or dilator tip, and the sheath 90 that housed the graft 30 was not peeled away. The use of the cartridge 200 thereby allows for delivery of the graft 60 into the graft 30 while limiting the possibility of contacting the branch extension prostheses 120 and 130, thereby limiting instances where the prostheses 120 and 130 can become damaged or crushed by traditional delivery systems using dilator tips and/or catheters.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A method for deploying an endoluminal prosthesis, the method comprising:
   delivering a first endoluminal prosthesis housed within a lumen of a delivery sheath through a patient's skin and to a body vessel, the delivery sheath having proximal and distal ends with the lumen extending therebetween;
   wherein the first endoluminal prosthesis has a compressed delivery state and an expanded state and is preloaded in the compressed delivery state within the delivery sheath and moveable proximally relative to the delivery sheath for delivery out of the proximal end of the delivery sheath;
   exposing the first endoluminal prosthesis from the proximal end of the delivery sheath at a target location within the body vessel;
   expanding the first endoluminal prosthesis into engagement with a wall of the body vessel;
   delivering a second endoluminal prosthesis to a distal opening of the delivery sheath, wherein the second endoluminal prosthesis is housed within a peel-away sheath having at least two portions, wherein the second endoluminal prosthesis has a compressed delivery state and an expanded state and is preloaded in its compressed delivery state in the peel-away sheath and moveable proximally relative to the peel-away sheath for delivery out of a proximal end of the peel-away sheath, wherein the peel-away sheath has a generally constant inner diameter such that the second endoluminal prosthesis has a preloaded shape that remains generally constant when moved within the peel-away sheath;
   wherein the proximal end of the peel-away sheath is sized and configured to mate with the distal end of the delivery sheath where the generally constant inner diameter of the peel-away sheath at the proximal end of the peel-away sheath generally corresponds to an inner diameter of the delivery sheath at the distal end of the delivery sheath so that the second endoluminal prosthesis is moveable in a proximal direction from within the peel-away sheath into the delivery sheath lumen while remaining in its compressed delivery state, wherein a shape of the second endoluminal prosthesis when moved into the delivery sheath generally corresponds to the preloaded shape;
   advancing the second endoluminal prosthesis proximally relative to the peel-away sheath and into the distal opening of the delivery sheath;
   while advancing the second endoluminal prosthesis, peeling away the at least two portions of the peel-away sheath;
   advancing the second endoluminal prosthesis proximally through the delivery sheath;
   exposing the second endoluminal prosthesis from the proximal end of the delivery sheath; and
   expanding the second endoluminal prosthesis.

2. The method of claim 1, wherein the second endoluminal prosthesis directly contacts an inner surface of the peel-away sheath when the second endoluminal prosthesis is being delivered to the distal opening of the delivery sheath.

3. The method of claim 2 further comprising contacting an inner surface of the delivery sheath with the second endoluminal prosthesis while it remains in contact with the peel-away sheath when the second endoluminal prosthesis is advancing into the delivery sheath.

4. The method of claim 1 further comprising partially peeling away the peel-away sheath with the second endoluminal prosthesis partially inserted into the delivery sheath.

5. The method of claim 4, wherein the second endoluminal prosthesis remains substantially covered by a combination of the peel-away sheath and the delivery sheath when the second endoluminal prosthesis is advancing into the delivery sheath.

6. The method of claim 1, wherein the second endoluminal prosthesis is advanced by advancing a pusher member in contact with a distal end of the second endoluminal prosthesis.

7. A method for deploying an endoluminal prosthesis, the method comprising:

delivering a first endoluminal prosthesis housed within a lumen of a delivery sheath through a patient's skin and to a body vessel, the delivery sheath having proximal and distal ends with the lumen extending therebetween;

wherein the first endoluminal prosthesis has a compressed delivery state and an expanded state and is preloaded in the compressed delivery state within the delivery sheath and moveable proximally relative to the delivery sheath for delivery out of the proximal end of the delivery sheath;

exposing the first endoluminal prosthesis from the proximal end of the delivery sheath at a target location within the body vessel;

retracting the proximal end of the delivery sheath distally away from a distal end of the first endoluminal prosthesis after exposing the first endoluminal prosthesis;

expanding the first endoluminal prosthesis into engagement with a wall of the body vessel;

delivering a second endoluminal prosthesis to a distal opening of the delivery sheath, wherein the second endoluminal prosthesis is housed within a peel-away sheath having at least two portions, wherein the second endoluminal prosthesis has a compressed delivery state and an expanded state and is preloaded in its compressed delivery state in the peel-away sheath and moveable proximally relative to the peel-away sheath for delivery out of a proximal end of the peel-away sheath, wherein the peel-away sheath has a generally constant inner diameter such that the second endoluminal prosthesis has a preloaded shape that remains generally constant when moved within the peel-away sheath;

wherein the proximal end of the peel-away sheath is sized and configured to mate with the distal end of the delivery sheath where the generally constant inner diameter of the peel-away sheath at the proximal end of the peel-away sheath generally corresponds to an inner diameter of the delivery sheath at the distal end of the delivery sheath so that the second endoluminal prosthesis is moveable in a proximal direction from within the peel-away sheath into the delivery sheath lumen while remaining in its compressed delivery state, wherein a shape of the second endoluminal prosthesis when moved into the delivery sheath generally corresponds to the preloaded shape;

advancing the second endoluminal prosthesis proximally relative to the peel-away sheath and into the distal opening of the delivery sheath;

while advancing the second endoluminal prosthesis, peeling away the at least two portions of the peel-away sheath;

advancing the second endoluminal prosthesis proximally through the delivery sheath;

exposing the second endoluminal prosthesis from the proximal end of the delivery sheath; and expanding the second endoluminal prosthesis into an overlapping engagement with the first endoluminal prosthesis.

8. The method of claim 7, further comprising advancing the proximal end of the delivery sheath into a lumen of the expanded first endoluminal prosthesis after expanding the first endoluminal prosthesis.

9. The method of claim 7, further comprising retracting the delivery sheath when exposing the second endoluminal prosthesis.

10. The method of claim 7, further comprising advancing a first guidewire prior to delivering the first endoluminal prosthesis housed within the lumen of the delivery sheath through the patient's skin and to the body vessel, delivering the first endoluminal prosthesis over the first guidewire, and delivering the second endoluminal prosthesis and peel-away sheath over the first guidewire.

11. The method of claim 7, wherein the first endoluminal prosthesis is coupled to a dilator tip as the first endoluminal prosthesis is delivered to the body vessel, the dilator tip is retracted from the body vessel after the first endoluminal prosthesis is delivered, and the second endoluminal prosthesis is delivered without the use of a dilator tip.

12. The method of claim 7, wherein the first endoluminal prosthesis is coupled to an inner catheter extending through a lumen of the first endoluminal prosthesis during delivery of the first endoluminal prosthesis, the inner catheter is withdrawn after the first endoluminal prosthesis is delivered, and the second endoluminal prosthesis is delivered without the use of a catheter extending therethrough.

13. A system for facilitating deployment of an endoluminal prosthesis, the system comprising:

a delivery sheath having proximal and distal ends and a lumen extending therebetween;

a first endoluminal prosthesis having a compressed delivery state and an expanded state and being preloaded in the compressed delivery state within the delivery sheath and moveable proximally relative to the delivery sheath for delivery out of the proximal end of the delivery sheath; and a second endoluminal prosthesis having a compressed delivery state and an expanded state and being preloaded in its compressed delivery state in a peel-away sheath and moveable proximally relative to the peel-away sheath for delivery out of a proximal end of the peel-away sheath, wherein the peel-away sheath has a generally constant inner diameter such that the second endoluminal prosthesis has a preloaded shape that remains generally constant when moved within the peel-away sheath;

wherein the proximal end of the peel-away sheath is sized and configured to mate with the distal end of the delivery sheath where the generally constant inner diameter of the peel-away sheath at the proximal end of the peel-away sheath generally corresponds to an inner diameter of the delivery sheath at the distal end of the delivery sheath so that the second endoluminal prosthesis is moveable in a proximal direction from within the peel-away sheath into the delivery sheath lumen while remaining in its compressed delivery state, wherein a shape of the second endoluminal prosthesis when moved into the delivery sheath generally corresponds to the preloaded shape.

14. The system of claim 13, wherein the first endoluminal prosthesis is coupled to a catheter extending through a lumen of the first endoluminal prosthesis and the second endoluminal prosthesis is not coupled to any catheter.

15. The system of claim 13, wherein the first endoluminal prosthesis is coupled to a dilator tip disposed proximally therefrom and the second endoluminal prosthesis is not coupled to any dilator tip.

16. The system of claim 15, wherein the first endoluminal prosthesis includes a stent coupled to a proximal end of a graft and further removably coupled to the dilator tip when the first endoluminal prosthesis is in its delivery state.

17. The system of claim 13, wherein the second endoluminal prosthesis contacts an inner surface of the peel-away sheath.

18. The system of claim 13, wherein the second endoluminal prosthesis includes a pair of leg portions at the distal end thereof.

19. The system of claim 13, wherein the distal end of the delivery sheath is coupled to a funnel member sized to receive the peel-away sheath when the second endoluminal prosthesis is in its delivery state.

20. The system of claim 13, wherein the peel-away sheath does not overlap the distal end of the delivery sheath when the peel-away sheath mates with the delivery sheath.

* * * * *